United States Patent [19]

Wilson

[11] Patent Number: 5,520,574
[45] Date of Patent: May 28, 1996

[54] DENTAL INSTRUMENT SHARPENING DEVICE

[76] Inventor: Roselyn Wilson, 11538 172nd St., Lakeville, Minn. 55044

[21] Appl. No.: 236,495

[22] Filed: Apr. 29, 1994

[51] Int. Cl.$^6$ ........................................ B23F 21/03
[52] U.S. Cl. ............................ 451/540; 451/321
[58] Field of Search ........................ 491/555, 554, 491/552, 540, 321, 320, 312; 451/45, 371, 319

[56] References Cited

U.S. PATENT DOCUMENTS

| | | | |
|---|---|---|---|
| 2,008,025 | 6/1934 | Luxmore | 451/321 |
| 3,436,870 | 4/1969 | Sellman | 451/540 |
| 4,838,899 | 6/1989 | Bifuk | 451/540 |

OTHER PUBLICATIONS

Photocopies of actual devices: "Prior Art A" being a ceramic Knife Sharpening Stone and Prior Art B being a India stone. Hand drawings of prior art as described above.

*Primary Examiner*—Bruce M. Kisliuk
*Assistant Examiner*—Andrew Weinberg
*Attorney, Agent, or Firm*—Palmatier, Sjoquist & Helget

[57] ABSTRACT

A device for sharpening dental instruments is disclosed. The device is particularly advantageous for sharpening and shaping dental curettes and universals. The device is comprised of a generally rectangular and elongate wedge-shaped ceramic stone. The stone has a planar front surface and a planar back surface, the surfaces are obliquely positioned with respect to each other. A rounded top lip and a rounded bottom lip join the front surface and the back surface. The top surface has a groove, semicircular in cross-section, extending lengthwise. The groove is sized to receive the toe portion of dental curettes or universals for sharpening and shaping.

13 Claims, 2 Drawing Sheets

DENTAL INSTRUMENT SHARPENING DEVICE

BACKGROUND OF THE INVENTION

This invention relates to dentistry, more particularly, it relates to a device for sharpening dental instruments such as curettes.

Dentists and dental hygienists utilize various types of hand-held instruments for examination, cleaning, and for performing dental work on patient's teeth. Such instruments include curettes, universals, scalers, and explorers. All of these dental instruments have an elongate shaft with workpieces extending out of the ends or collars of said shafts. The scalers and explorers have a sharp pointed tip on the workpiece. The curettes and universals have a rounded and flat tip, at least one sharpened cutting edge adjacent to the tip, and a widthwise curvature on a bottom surface. The tips and cutting edges on such instruments become dull with use and require periodic shaping and sharpening. In that the work-tips are extremely small, the proper shaping and sharpening of said work-tips is an extremely delicate and difficult task. The cutting edge on curettes or universals is formed by the junction between a substantially flat lateral side and a curved top face. The lateral side may be conveniently shaped with a planar surface, however, the curved top surface is much more difficult to shape and sharpen. Previously, general purpose sharpening stones have been utilized. Such stones are typically rectangular and do not have the appropriate combination of concave and convex curvatures for sharpening the curettes or universals with maximum efficiency and expediency. Additionally, the prior art was typically comprised of conventional sharpening stones which require oil or water for use.

No known prior art devices exist which are wedge-shaped with a concave groove for shaping the widthwise curvature of the toe of the curettes and a convex surface sized for shaping the face of curettes.

None of the prior art shows a groove specifically designed and sized for receiving and sharpening the toe of dental curettes.

SUMMARY OF THE INVENTION

A device for sharpening dental instruments is disclosed. The device is particularly advantageous for sharpening and shaping dental curettes and universals. The device is comprised of a generally rectangular and elongate wedge-shaped ceramic stone. The stone has a planar front surface and a planar back surface, the surfaces are obliquely positioned with respect to each other. A rounded top lip and a rounded bottom lip join the front surface and the back surface. The top surface has a groove, semicircular in cross-section, extending lengthwise. The groove is sized to receive the toe portion of dental curettes or universals for sharpening and shaping.

An object and advantage of the invention is that suitable concave and convex surfaces are provided on the sharpening stone suitable for the concave and convex curvatures found on dental curettes.

An additional object and advantage of the invention is that the ceramic material with aluminum oxide has a high surface tension allowing sharpening of the dental instruments without the use of water or oil as is necessary with conventional stones.

DETAILED DESCRIPTION OF THE PREFERRED EMBODIMENTS

Figure 1:
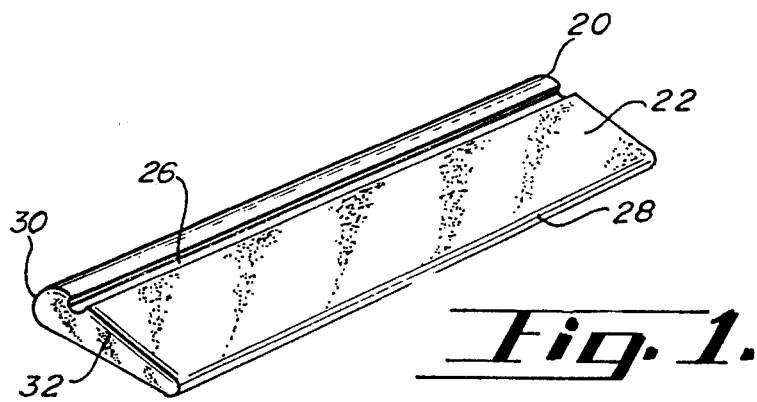
FIG. 1 is a perspective view of the front surface and lower lip of the device.
Figure 3:
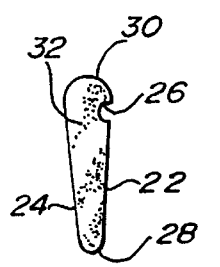
FIG. 3 is an end view of the device showing the semicircular groove.
Figure 4:
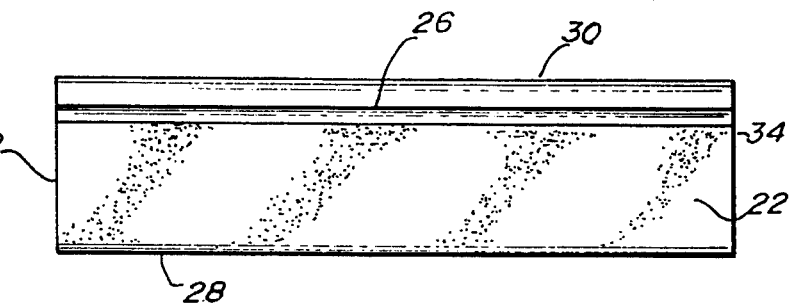
FIG. 4 is a plan view of the device.
Figure 2:
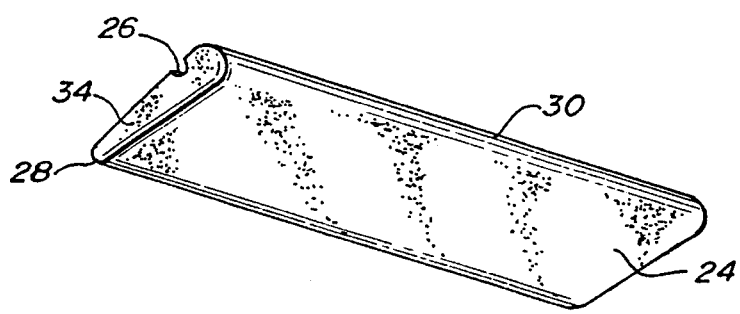
FIG. 2 is a perspective view showing the bottom surface and the upper lip of the device.

Referring to FIGS. 1–4, two perspectives, an end view and a top view, of the device are shown. The device is generally indicated by the numeral 20. As depicted, the device is generally wedge-shaped with a planar top surface 22 and a planar bottom surface 24. A substantially semicircular groove 26 extends the length of the device on the top surface 22. The groove 26 is positioned near the upper lip 30 in that the thickness of the device 20 is greatest in this region providing maximum resistance to breakage along the groove 26. The top surface 22 and the bottom surface 24 converge at a lower lip 28 and also join at an upper lip 30. The device has two planar ends 32, 34. Please note that the positional references of the various elements such as top, bottom, upper and lower are only for descriptive and reference purposes and it is understood that the device does not have a specific upright or other required orientation.

The device in the preferred embodiment is comprised of a aluminum oxide ceramic material formed by conventional extrusion means. The groove 26 is most easily formed after extrusion and prior to the curing of the material.

Figure 5:
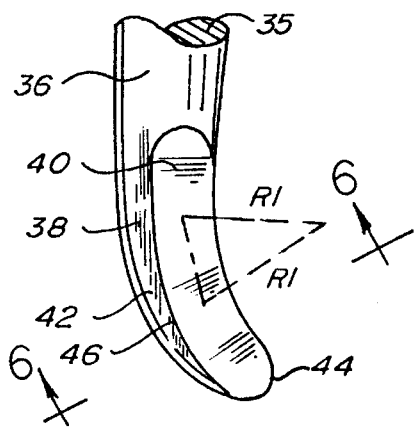
FIG. 5 is a perspective view of a toe of the dental curette.

Referring to FIG. 5, a workpiece 35 of a dental instrument, specifically a curette, is shown in perspective with a work-tip 36 and a toe portion 38. The toe portion 38 has a face 40, a lateral side 42 and a frontal edge 44. The frontal edge 44 extends up the work-tip 36 to form a cutting edge 46 defined by the junction of the lateral surface 42 and the face 40. The face 40 has a lengthwise radius of curvature designated by the letter R1 and a width generally defined as the distance from the lateral side 42 to the edge 50.

Figure 6:
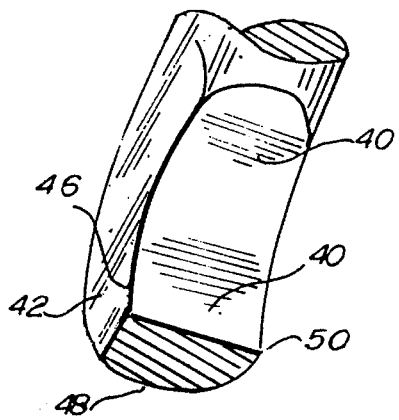
FIG. 6 is a cross-sectional view taken at plane 6—6 of FIG. 5.

Referring to FIG. 6, a cross-sectional of the work-tip 36 is shown taken at plane 6—6 of FIG. 5. FIG. 6 shows that the lateral side 42 is substantially flat permitting shaping with a planar surface. Also denoted is a back surface 48. The face 40 is a curved surface that intersects the lateral face 42 at an angle of approximately 90° on this particular instrument. The edge 50 located opposite of the cutting edge 46 is not sharpened in that it is not a cutting edge in standard curettes. If the instrument depicted were a universal type dental instrument this edge would also be a cutting edge similar to cutting edge 46. The width of the toe portion is defined for the purpose of this application as extending between lateral side 42 and the opposite edge 50.

With reference to FIGS. 5 and 6, the portions of the work-tip 36 that require periodic sharpening are the front edge 44 and the cutting edge 46 and also edge 50 if the instrument is of a universal type. Sharpening said edges necessarily requires shaping of the face 40, the lateral side 42, and the back side 48.

Figure 7:
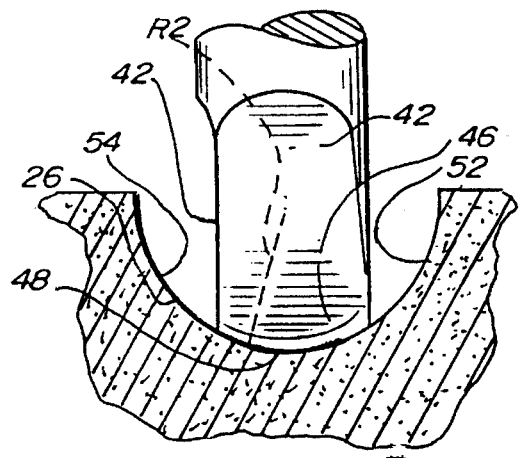
FIG. 7 is a partial cross-sectional view of the sharpening device at the semicircular groove showing the dental curette toe with the device.

Referring to FIG. 7, a partial sectional view of the device 20 through the groove 26 with work-tip 36 engaged for sharpening. The groove 26 has an inner concave surface 52 with concave curvature or a radius designated by R2. The toe portion 38 of the work-tip 36 ideally has a substantially identical widthwise curvature or radius on the back surface 48 of the workpiece. This radius or curvature is also identified by R2.

Figure 8:
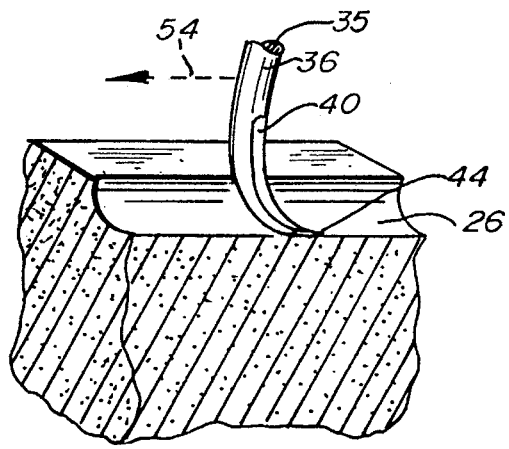
FIG. 8 is another partial sectional view taken through the groove lengthwise showing the engagement of the toe of the dental curette with the device.

Referring to FIG. 8, a partial sectional view of the device 20 is shown with a work-tip 36 engaged for sharpening. The work-tip 36 is generally slid or rubbed in a lengthwise direction inside the groove 26 in the direction as indicated by the arrow 54. In this view the back surface 48 of the work-tip 36 is being shaped and the frontal edge 44 is thereby sharpened. The groove 26 can also be utilized for shaping the lateral side 42 by appropriately tilting the instrument whereby the lateral side 42 engages the upper concave surface 54 which is best shown in FIG. 7. Additionally, the lateral face may be shaped by way of the planar top surface 22, the planar bottom surface 24, or the planar end surfaces 32, 34.

Figure 9:
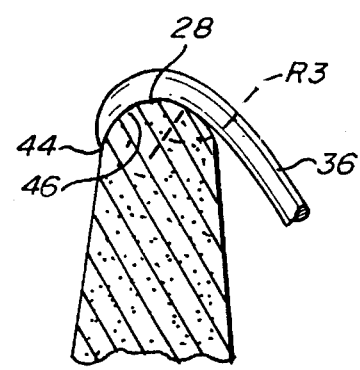
FIG. 9 is a cross-sectional view of the device taken through the lower lip and showing the engagement of the dental curette workpiece at the face.

To complete the sharpening of the workpiece 35, the face 40 must also be shaped. FIG. 9 shows a cross-sectional taken of the device through the lower lip 28. The lower lip 28 has a radius or curvature as identified by R3 which is sized to substantially match or be slightly smaller then the radius or curvature R1 of the face 40 as shown in FIG. 5. The face 40 may be shaped by way of any convenient motion of the device 20, either lateral, circular, or longitudinal with respect to the work-tip 36.

The appropriately sized concave and convex surfaces of the device provide an expedient and precise means of sharpening dental instruments. Similarly, the points of scalers and explorers may be conventionally sharpened on the planar surfaces 22, 24, 32, 34 of the device or groove 26. The groove is suitably two and one quarter to two and one half curette toe widths in diameter.

Dental curettes typically have a width of 0.03 to 0.38 millimeters. A suitable radius for the groove 26 is 0.045 inches. A suitable radius for the lower lip is 0.070 inches which sufficiently matches the face curvature of most curettes. A suitable radius for the upper lip is 0.125 inches.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed is:

1. A device for sharpening a dental instrument, the device comprised of a stone generally wedge-shaped and elongate, the stone having a planar top surface, a planar bottom surface obliquely positioned with respect to the top surface, an upper lip and a lower lip joining the top surface and bottom surface, the lower lip parallel to the upper lip, and a semicircular groove extending lengthwise on the top surface.

2. The device of claim 1, wherein the stone is an aluminum oxide ceramic.

3. The device of claim 1, wherein the dental instrument is a dental curette comprised of a handle and a work-tip with a toe portion, the toe portion having a width, and wherein the semicircular groove of the stone has a diameter of substantially two and one-half to three curette toe widths.

4. The device of claim 1, wherein the dental instrument is a dental curette comprised of a handle and a work-tip with a toe portion, the toe portion having a widthwise curvature, and wherein the semicircular groove of the stone has a concave curvature substantially corresponding to the widthwise curvature for engaging the toe portion.

5. The device of claim 1, wherein the dental instrument is a dental curette comprised of a handle and a work-tip, the work tip having a shank and a face portion with a curvature, and wherein the lower lip of the stone has a curvature substantially equivalent to the curvature of the face portion.

6. The device of claim 1 wherein the upper lip and lower lip both have radii of curvature and the upper lip has a greater radii of curvature than the lower lip and wherein the groove is positioned in proximity to the upper lip on the top surface.

7. A device for sharpening a dental instrument having a toe portion with a lengthwise convex curvature, the device comprised of a stone generally wedge-shaped and elongate, the stone having a planar front surface, a planar back surface obliquely positioned with respect to the front surface, a top lip joining the front surface and the back surface, a bottom lip opposite to the top lip, the top lip joining the front surface and the back surface, and a groove extending lengthwise on the front surface, the groove having a concave curvature sized for the convex curvature of the dental instrument.

8. The device of claim 7, wherein the dental instrument is a dental curette comprised of a handle and a work-tip, the work tip having a shank and a toe portion, the toe portion having a face with an internal radius, and wherein the bottom lip of the stone has a radius substantially equal to the internal radius of the face.

9. The device of claim 8, wherein the stone is formed of a ceramic material with suspended aluminum oxide.

10. The device of claim 9, wherein the dental instrument is a dental curette and the toe portion has a widthwise convex curvature and wherein the semicircular groove has a concave surface sized for said widthwise curvature.

11. The device of claim 10, wherein the dental instrument is a dental curette comprised of a handle and a work-tip, the work-tip having a shank and a face portion with a lengthwise curvature, and wherein the bottom lip of the stone has a curvature substantially equivalent to the curvature of the face portion.

12. The device of claim 1, wherein the dental instrument is a dental curette comprised of a handle and a work-tip, the work-tip having a shank and a toe portion, the toe portion having a face with an internal radius, and wherein the bottom lip of the stone has a radius substantially equal to the internal radius of the face.

13. A device for sharpening a dental instrument, the device comprised of a stone generally wedge-shaped and elongate, the stone having a planar front surface, a planar back surface obliquely positioned with respect to the front surface, a convex upper lip extending from the front surface to the back surface, a convex lower lip opposite to the upper lip and extending from the front surface to the back surface, and a semicircular groove extending lengthwise on the top front surface.

* * * * *

UNITED STATES PATENT AND TRADEMARK OFFICE
CERTIFICATE OF CORRECTION

PATENT NO. : 5,520,574
DATED : May 28, 1996
INVENTOR(S) : Roselyn Wilson

It is certified that error appears in the above-indentified patent and that said Letters Patent is hereby corrected as shown below:

Column 4, line 64, please delete the word "top".

Signed and Sealed this

Thirtieth Day of July, 1996

Attest:

BRUCE LEHMAN

Attesting Officer

Commissioner of Patents and Trademarks